(12) United States Patent
Dahanukar et al.

(10) Patent No.: US 9,051,291 B2
(45) Date of Patent: Jun. 9, 2015

(54) PROCESS FOR PRODUCING (S)-EQUOL

(71) Applicant: DR. REDDY'S LABORATORIES LIMITED, Hyderabad (IN)

(72) Inventors: Vilas Hareshwar Dahanukar, Hyderabad (IN); Syam Kumar Unniaran Kunhimon, Thrissur (IN); Upadhya Timmana, Secunderabad (IN); Abir Kumar Pal, Shantiniketan (IN); Mahendar Macha, Medak (IN); Venkata Madhubabu Meesala, Kakinada (IN); Krishna Mohan Thalabathula, Hyderabad (IN); Shankar Ramanathan, Salem (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 14/384,625

(22) PCT Filed: Mar. 27, 2013

(86) PCT No.: PCT/IB2013/052428
§ 371 (c)(1),
(2) Date: Sep. 11, 2014

(87) PCT Pub. No.: WO2013/144857
PCT Pub. Date: Oct. 3, 2013

(65) Prior Publication Data
US 2015/0057456 A1    Feb. 26, 2015

(30) Foreign Application Priority Data
Mar. 28, 2012   (IN) ............................ 1197/CHE/2012

(51) Int. Cl.
| C07C 39/15 | (2006.01) |
| C07C 57/38 | (2006.01) |
| C07D 311/76 | (2006.01) |
| C07D 311/04 | (2006.01) |
| C07C 59/52 | (2006.01) |
| C07C 211/27 | (2006.01) |

(52) U.S. Cl.
CPC .............. *C07D 311/04* (2013.01); *C07C 59/52* (2013.01); *C07C 211/27* (2013.01)

(58) Field of Classification Search
CPC ........ C07C 39/15; C07C 57/38; C07D 311/76
See application file for complete search history.

(56) References Cited
U.S. PATENT DOCUMENTS
2012/0094336 A1    4/2012    Steffan

OTHER PUBLICATIONS

International Search Report dated Sep. 12, 2013, for corresponding International Patent Application No. PCT/IB2013/052428.

Written Opinion dated Sep. 12, 2013, for corresponding International Patent Application No. PCT/IB2013/052428.

Muthyala et al., "Equol, a natural estrogenic metabolite from soy isoflavones: convenient preparation and resolution of R- and 5-equols and their differing binding and biological activity through estrogen receptors alpha and beta", Bioorganic and Medicinal Chemistry, 2004, pp. 1559 to 1567, vol. 12, Elsevier Ltd.

(Continued)

*Primary Examiner* — Bruck Kifle
(74) *Attorney, Agent, or Firm* — Pergament Gilman & Cepeda LLP; Edward D. Pergament; Milagros A. Cepeda

(57) ABSTRACT

The present application relates to an improved process for the preparation of (S)-equol (1). The present application also relates to novel intermediates of formula (7), (7A), (8) and (9) and their use for the synthesis of (S)-equol.

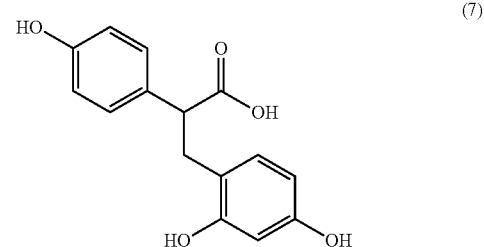

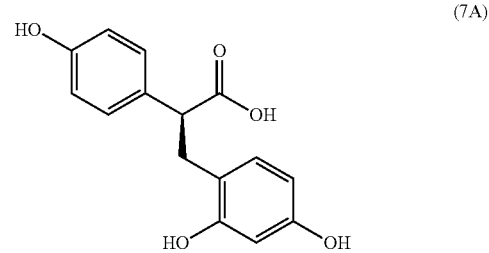

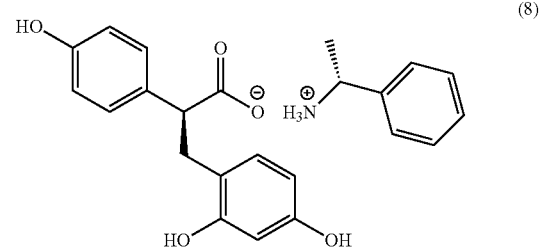

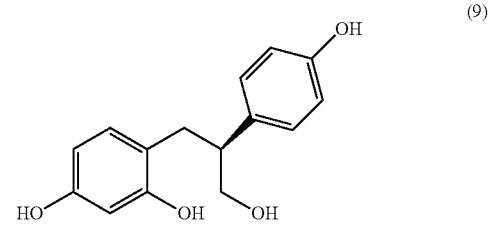

13 Claims, No Drawings

(56) References Cited

OTHER PUBLICATIONS

Heemstra et al., "Total Synthesis of (S)-Equol", Organic Letters, 2006, pp. 5441 to 5443, vol. 8—issue No. 24, American Chemical Society.

Takashima and Kobayashi, "New synthetic route to (S)-(−)-equol through allylic substitution", Tetrahedron Letters, 2008, pp. 5156 to 5158, vol. 49, Elsevier Ltd.

Takashima et al., "Synthetic access to optically active isoflavans by using allylic substitution", Tetrahedron, 2010, pp. 197 to 207, vol. 66, Elsevier Ltd.

PROCESS FOR PRODUCING (S)-EQUOL

This application is a National Stage Application under 35 U.S.C. §371 of PCT International Application No. PCT/IB2013/052428 filed Mar. 27, 2013, which claims the benefit of Indian Provisional Application No. 1197/CHE/2012, filed Mar. 28, 2012, all of which are hereby rated by reference in their entireties.

FIELD OF INVENTION

The present application relates to an improved process for the production of (S)-equol (1). The present application also relates to substantially pure (S)-equol (1).

INTRODUCTION (S)-Equol (1) is chemically known as 4",7-isoflavandiol. It is produced in the human intestine by bacterial metabolism of daidzein (2). However, only about 30-50% of human population has daidzein to equol converting bacteria. (S)-Equol (1) binds to estrogen receptor-β and is believed to be useful in the prevention of prostate cancer. (S)-Equol (1) is also believed to be responsible for maintaining bone health and physiological changes during menopause.

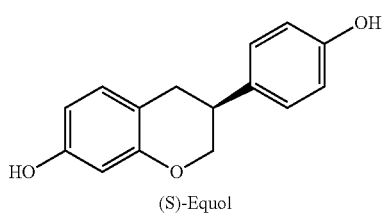
(S)-Equol (1)

Daidzein (2)

Takashima et al. (Tetrahedron Letters, 2008, 49, 5156-5158) discloses a process for the preparation of (S)-Equol (1) starting from naturally occurring ethyl lactate. The disclosed process is an eleven-step process and the total yield obtained by the process is only 31.6%. Also, (S)-Equol (1) produced by this method has low enantiomeric purity of 91%.

Takashima et al. (Tetrahedron Letters, 2010, 66, 197-207) further discloses a process for the preparation of (S)-Equol (1) starting from 2,4-dimethoxy benzaldehyde. (S)-Equol (1) produced by this method has also enantiomeric purity of 91%.

Muthyala et al. (Bioorganic & Medicinal Chemistry, 2004, 12, 1559-1567) teaches a process for the preparation of (S)-Equol (1). The process involves the reduction of daidzein (2) by ammonium formate in presence of palladium-charcoal to produce racemic equol. The racemic equol is then resolved into enantiomerically pure isomer by chiral liquid chromatography. The process is not acceptable for commercial preparation of (S)-Equol (1) as it requires chiral liquid chromatography technique to separate the enantiomers of racemic equol.

Hemstra et al. (Organic Letters, 2006, 8, 5441-5443) discloses a process for the preparation of (S)-Equol (1) starting from 2-bromo-4-methoxy benzyl chloride. Although the process produces about 99.9% enantiomerically pure (S)-Equol (1), the main disadvantage of the process is its poor yield i.e., only 9.8%.

The prior art processes for the synthesis of (S)-Equol (1) are not suitable for commercial production because of their low yield and/or low enantiomeric purity of the product. Hence, there is a need in the art for an efficient process for the preparation of (S)-Equol (1).

SUMMARY

One embodiment of the present application relates to a process for the preparation of (S)-equol (1)

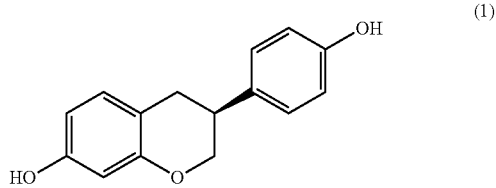 [SMILES: Oc1ccc([C@H]2COc3cc(O)ccc3C2)cc1]

comprising:
(a) reacting 4-hydroxy phenyl acetic acid and 2,4-dihydroxy benzaldehyde in presence of an acid anhydride and a base to provide 4-(7-acetoxy-2-oxo-2H-chromen-3-yl)phenyl acetate of formula (3)

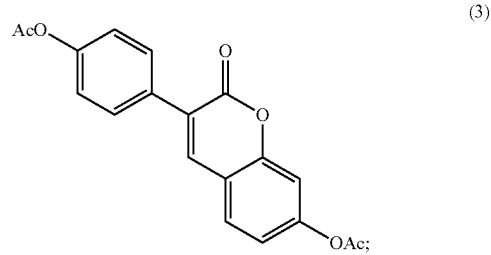 [SMILES: CC(=O)Oc1ccc(-c2cc3ccc(OC(C)=O)cc3oc2=O)cc1]

(b) hydrolyzing the acetyl groups of 4-(7-acetoxy-2-oxo-2H-chromen-3-yl)phenyl acetate of formula (3) in presence of a base to provide 7-hydroxy-3-(4-hydroxyphenyl)-2H-chromen-2-one of formula (4)

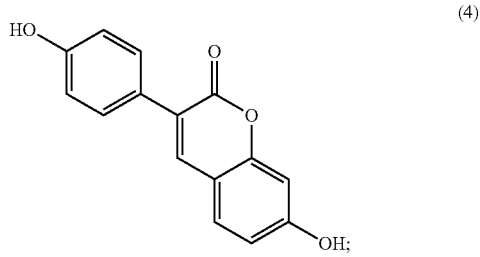 [SMILES: O=c1oc2cc(O)ccc2cc1-c1ccc(O)cc1]

(c) hydrogenating 7-hydroxy-3-(4-hydroxyphenyl)-2H-chromen-2-one of formula (4) to provide a mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6)

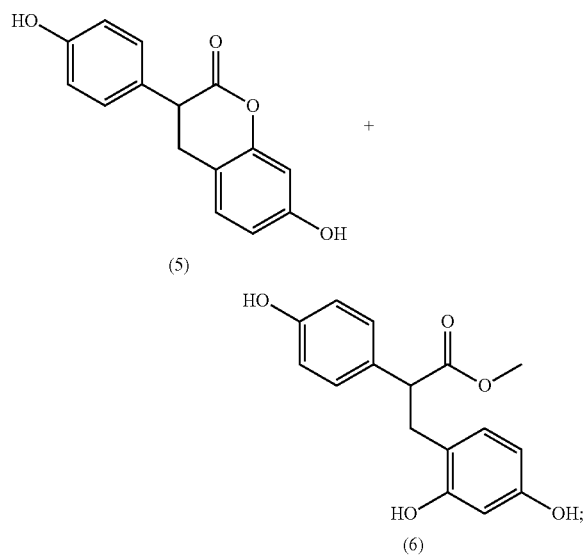

(d) hydrolyzing the mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6) by a base to provide 3-(2,4-dihydroxyphenyl)-2-(4-hydroxyphenyl)propanoic acid of formula (7)

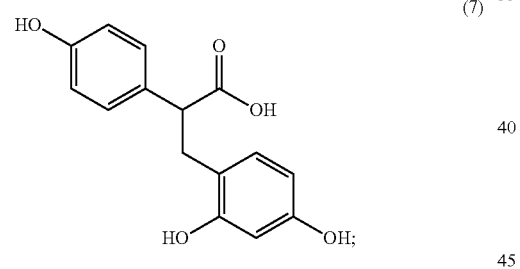

(e) resolving 3-(2,4-dihydroxyphenyl)-2-(4-hydroxyphenyl)propanoic acid of formula (7) to its corresponding (S)-isomer (7A) via diastereomeric salt formation with a chiral amine

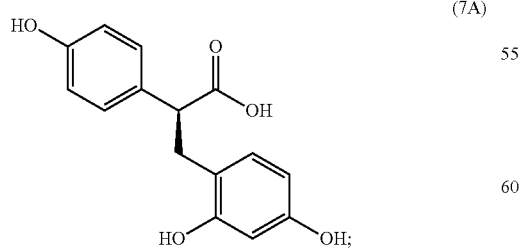

(f) reducing (S)-3-(2,4-dihydroxyphenyl)-2-(4-hydroxyphenyl)propanoic acid of formula (7A) to provide (S)-4-(3-hydroxy-2-(4-hydroxyohenyl)propyl)benzene-1,3-diol of formula (9)

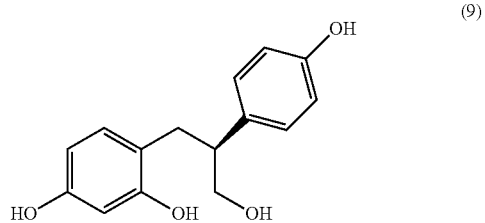 [SMILES: OC[C@@H](Cc1ccc(O)cc1O)c1ccc(O)cc1]

and (g) cyclizing (S)-4-(3-hydroxy-2-(4-hydroxyohenyl)propyl)benzene-1,3-diol of formula (9) to provide (S)-equol (1).

In another embodiment the present invention relates to compound of formula (7) and its use for synthesis of (S)-Equol (1)

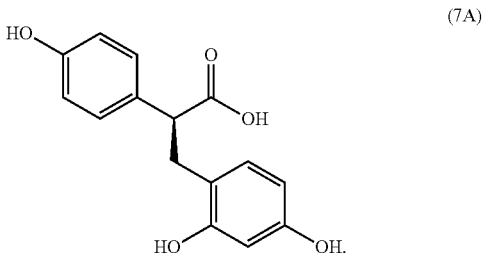 [SMILES: O=C(O)[C@@H](Cc1ccc(O)cc1O)c1ccc(O)cc1]

In yet another embodiment the present invention relates to compound of formula (7A) and its use for synthesis of (S)-Equol (1)

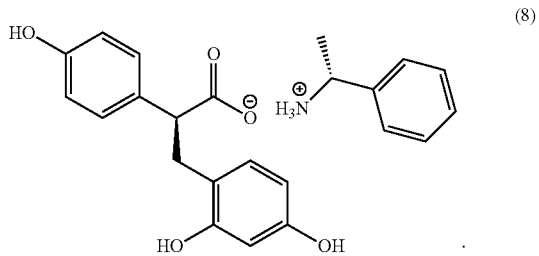

In still another embodiment the present invention relates to compound of formula (8) and its use for synthesis of (S)-Equol (1)

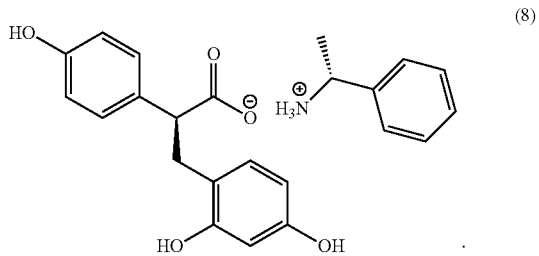

In another embodiment the present invention relates to compound of formula (9) and its use for synthesis of (S)-Equol (1)

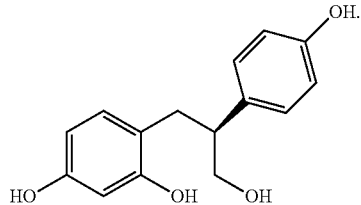
(9)

In still another embodiment the present application relates to a pharmaceutical composition comprising (S)-Equol (1).

DETAILED DESCRIPTION

One embodiment of the present application relates to a process for the preparation of (S)-equol (1)

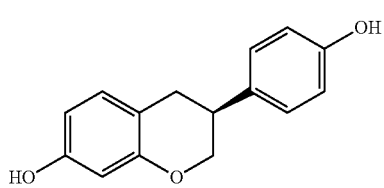
(1)

comprising:
(a) reacting 4-hydroxy phenyl acetic acid and 2,4-dihydroxy benzaldehyde in presence of an acid anhydride and a base to provide 4-(7-acetoxy-2-oxo-2H-chromen-3-yl)phenyl acetate of formula (3)

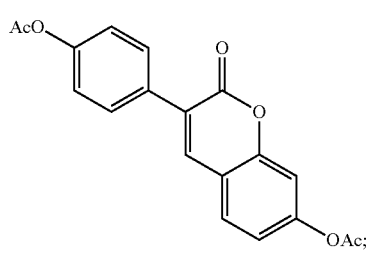
(3)

(b) hydrolyzing the acetyl groups of 4-(7-acetoxy-2-oxo-2H-chromen-3-yl)phenyl acetate of formula (3) in presence of a base to provide 7-hydroxy-3-(4-hydroxyphenyl)-2H-chromen-2-one of formula (4)

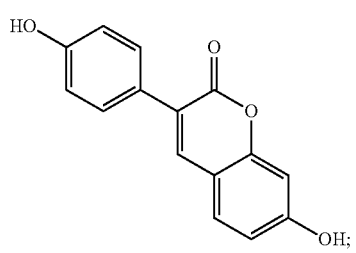
(4)

(c) hydrogenating 7-hydroxy-3-(4-hydroxyphenyl)-2H-chromen-2-one of formula (4) to provide a mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6)

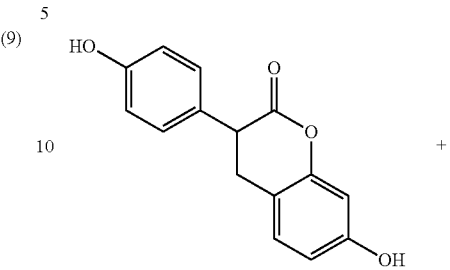
(5)

(6)

(d) hydrolyzing the mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6) by a base to provide 3-(2,4-dihydroxyphenyl)-2-(4-hydroxyphenyl)propanoic acid of formula (7)

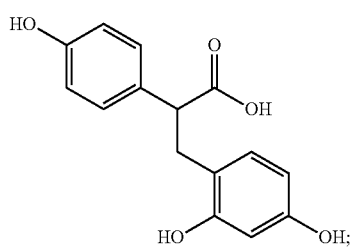
(7)

(e) resolving 3-(2,4-dihydroxyphenyl)-2-(4-hydroxyphenyl) propanoic acid of formula (7) to its corresponding (S)-isomer (7A) via diastereomeric salt formation with a chiral amine

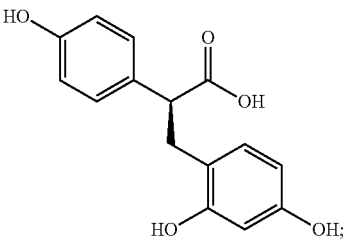
(7A)

(f) reducing (S)-3-(2,4-dihydroxyphenyl)-2-(4-hydroxyphenyl)propanoic acid of formula (7A) to provide (S)-4-(3- hydroxy-2-(4-hydroxyohenyl)propyl)benzene-1,3-diol of formula (9)

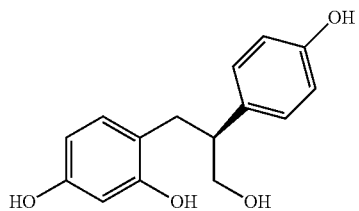

(9)

and (g) cyclizing (S)-4-(3-hydroxy-2-(4-hydroxyohenyl)propyl) benzene-1,3-diol of formula (9) to provide (S)-equol (1).

The schematic representation of the instant process for the preparation of (S)-equol (1) is shown in Scheme I.

Scheme I: Instant Process for preparation of (S)-equol (1)

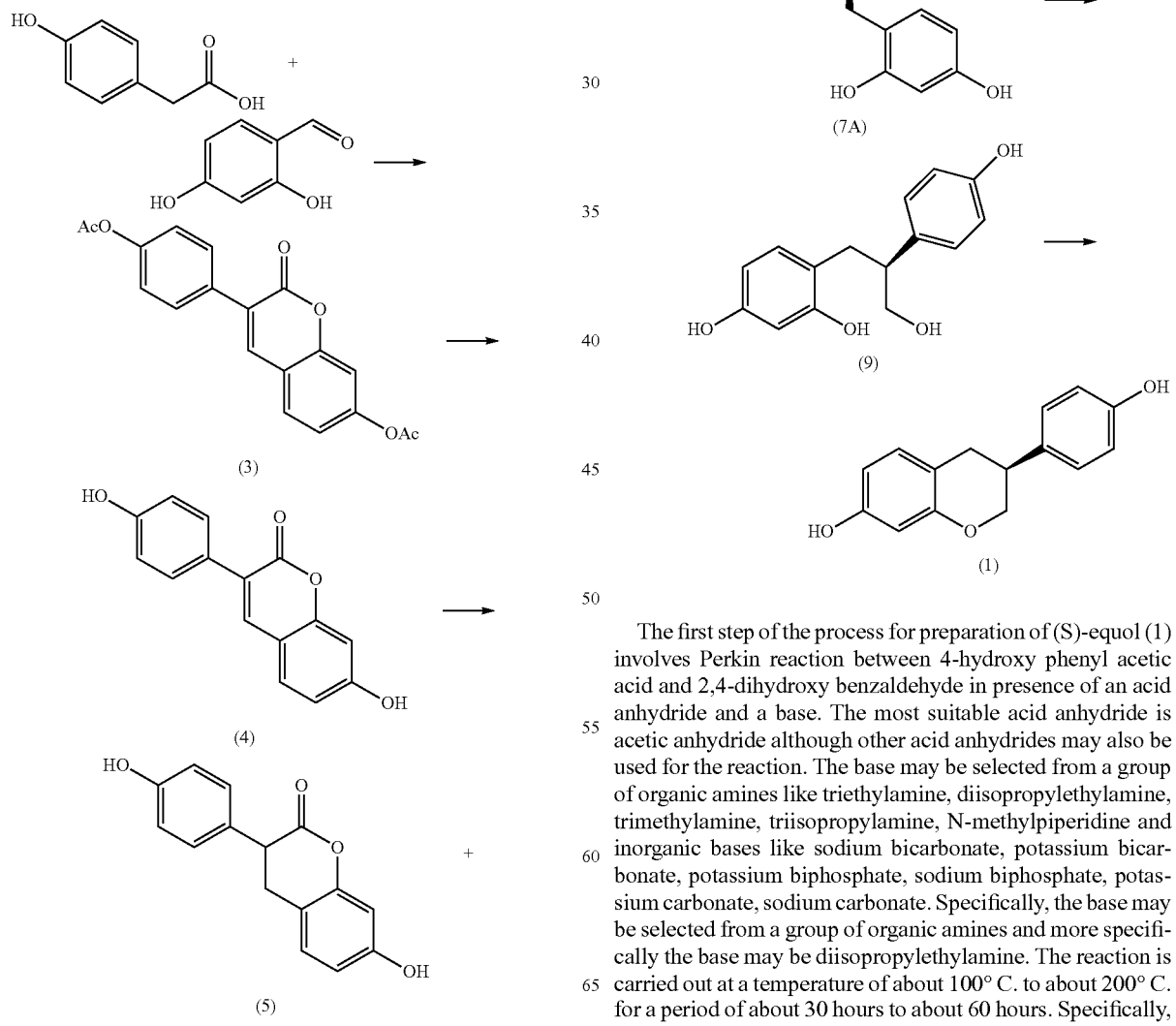

The first step of the process for preparation of (S)-equol (1) involves Perkin reaction between 4-hydroxy phenyl acetic acid and 2,4-dihydroxy benzaldehyde in presence of an acid anhydride and a base. The most suitable acid anhydride is acetic anhydride although other acid anhydrides may also be used for the reaction. The base may be selected from a group of organic amines like triethylamine, diisopropylethylamine, trimethylamine, triisopropylamine, N-methylpiperidine and inorganic bases like sodium bicarbonate, potassium bicarbonate, potassium biphosphate, sodium biphosphate, potassium carbonate, sodium carbonate. Specifically, the base may be selected from a group of organic amines and more specifically the base may be diisopropylethylamine. The reaction is carried out at a temperature of about 100° C. to about 200° C. for a period of about 30 hours to about 60 hours. Specifically, the reaction is carried out at a temperature of about 90° C. to about 150° C. for a period of about 35 hours to about 45 hours and more specifically the reaction is carried out at a temperature of about 115° C. to about 120° C. for a period of about 38 hours to about 42 hours. After the reaction is completed, the reaction mixture is cooled from about 10° C. to about 30° C. and specifically from about 20° C. to about 25° C. and water is added. The precipitated solid is filtered and washed with water and optionally dried to provide 4-(7-acetoxy-2-oxo-2H-chromen-3-yl)phenyl acetate of formula (3).

The acetyl groups of compound of formula (3) are hydrolyzed in presence of a base in the next step. The base may be selected from a group of lithium hydroxide, potassium hydroxide, sodium hydroxide, potassium carbonate, magnesium carbonate, sodium carbonate, sodium bicarbonate and potassium bicarbonate. Specifically, the base is lithium hydroxide. The solvent for the hydrolysis reaction may be selected from a group of water, alcohols, tetrahydrofuran (THF), acetonitrile (ACN), dimethyl formamide (DMF), dimethyl sulfoxide (DMSO) and a mixture thereof. Specifically, water is used as solvent. The hydrolysis reaction is carried out at a temperature of about 30° C. to about 100° C. for a period of about 30 minutes to about 5 hours. Specifically, the reaction is carried out at a temperature of about 50° C. to about 80° C. for a period of about 1 hour to about 4 hours and more specifically the reaction is carried out at a temperature of about 60° C. to about 70° C. for a period of about 1 hour to about 2 hours. After the completion of the reaction, the reaction mixture is diluted by the addition of water and acidified by adding an aqueous solution of an acid. The acid may be selected from a group of acetic acid, hydrochloric acid, sulfuric acid, oxalic acid, nitric acid, phosphoric acid and hydrobromic acid, specifically hydrochloric acid. The precipitated solid is collected by filtration and optionally dried to afford 7-hydroxy-3-(4-hydroxyphenyl)-2H-chromen-2-one of formula (4).

The compound of formula (4) is then hydrogenated to provide a mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6). The compound of formula (4) may be dissolved in a suitable solvent selected from the group of alcohols, DMF, dimethyl acetamide, N-methylpyrrolidine, THF, DMSO, acetonitrile and a mixture thereof. Specifically, the solvent is selected from a group of alcohols, DMF and a mixture thereof. The alcohols may be selected from a group of methanol, ethanol, isopropanol (IPA), tert-butanol and amyl alcohol. Specifically, the suitable solvent for hydrogenation is methanol. The hydrogenation is performed in presence of a heterogeneous catalyst selected from a group of palladium on solid carrier, Raney nickel, platinum, rhodium and ruthenium. The solid carrier may be for example carbon. Specifically, the heterogeneous catalyst is palladium on charcoal. The hydrogenation is carried out at about 5 bar to about 15 bar of hydrogen pressure at about 30° C. to about 100° C. for a period of about 5 hours to about 24 hours. Specifically, the hydrogenation is carried out at about 7 bar to about 12 bar of hydrogen pressure at about 40° C. to about 80° C. for a period of about 7 hours to about 15 hours and more specifically the hydrogenation is carried out at about 8 bar to about 10 bar of hydrogen pressure at about 60° C. to about 65° C. for a period of about 10 hours to about 12 hours. After the reaction is complete, the reaction mixture is filtered to remove the catalyst and the filtrate is distilled off to provide a mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6). The resulted product is carried forward for the next reaction without further purification.

The mixture of compound of formula (5) and compound of formula (6) is hydrolyzed in presence of a base to afford 3-(2,4-dihydroxyphenyl)-2-(4-hydroxyphenyl)propanoic acid of formula (7). The base may be selected from a group of potassium hydroxide, sodium hydroxide, lithium hydroxide, sodium carbonate, potassium carbonate, magnesium carbonate, potassium bicarbonate, sodium bicarbonate and a mixture thereof. Specifically, the base is potassium hydroxide. The solvent for the hydrolysis reaction may be selected from a group of water, alcohols, THF, acetonitrile, DMF, DMSO and a mixture thereof. Specifically, the solvent is water. The hydrolysis is carried out at a temperature of about 0° C. to about 50° C. Specifically, the hydrolysis is carried out at a temperature below 20° C. After the completion of the reaction, the reaction mixture is acidified by adding an acid. The acid may be selected from a group of hydrochloric acid, sulfuric acid, nitric acid, phosphoric acid, acetic acid and hydrobromic acid. Specifically, the acid is hydrochloric acid. The pH of the reaction mixture is adjusted from about 1 to about 4. Specifically, the pH of the reaction mixture is adjusted from about 2 to about 3. The product is extracted with an organic solvent which is immiscible in water. The organic solvent may be selected from a group of esters, ethers and hydrocarbon solvents. Specifically, the organic solvent is an ester. More specifically, the organic solvent is ethyl acetate. The organic solvent is distilled off under vacuum to provide 3-(2,4-dihydroxyphenyl)-2-(4-hydroxyphenyl)propanoic acid of formula (7).

One preferred embodiment of the present application relates to 3-(2,4-dihydroxyphenyl)-2-(4-hydroxyphenyl)propanoic acid of formula (7)

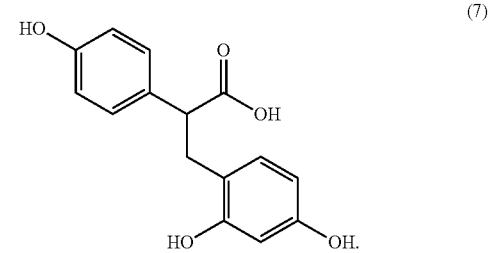 [SMILES: O=C(O)C(Cc1ccc(O)cc1O)c1ccc(O)cc1]

Another preferred embodiment of the present application relates to use of 3-(2,4-dihydroxyphenyl)-2-(4-hydroxyphenyl)propanoic acid of formula (7) in the preparation of (S)-equol (1).

The racemic acid of formula (7) may be resolved into its enantiomers by forming a diastereomeric salt with a chiral amine. The chiral amine may be selected from a group of α-methylbenzylamine, N-octyl-D-glucamine, L-prolinol, cinchonidine, cinchonine, N-Boc-3-amino piperidine and 3-amino piperidine. Specifically, the chiral amine is α-methylbenzylamine. The racemic acid of formula (7) and the chiral amine is dissolved in a suitable solvent at suitable condition. The solvent may be selected from a group of ethers, alcohols, water, hydrocarbons and mixture thereof. Specifically, the solvent is selected from a group of methanol, ethanol, isopropanol, tet-butanol, diethyl ether, diisopropyl ether, methyl tert-butyl ether, 1,4-dioxane, tetrahydrofuran, toluene, heptane, hexane, water and mixture thereof. More specifically, the solvent is an alcohol and most specifically, the solvent is isopropanol. The reaction mass is heated to a temperature of about 40° C. to about 80° C. and specifically from about 50° C. to about 70° C. More specifically, the reaction mass is heated to a temperature of about 55° C. to about 65° C. The reaction is maintained for about 30 minutes to about 2 hours and specifically the reaction mass is maintained for about 45 minutes to about 1.5 hours. More specifically, the reaction mass is maintained for about 1 hour. The reaction mass is cooled from about 0° C. to about 30° C. and specifically the reaction mass is cooled from about 15° C. to about 25° C. The reaction mass is maintained at this temperature for a period of about 2 hours to about 10 hours. Specifically, the reaction mass is maintained at this temperature for a period of about 4 hours to about 8 hours and more specifically the reaction mass is maintained at this temperature for a period of about 5 hours to about 6 hours. The resulting diastereomeric salt of (S)-3-(2,4-dihydroxyphenyl)-2-(4-hydroxyphenyl)propanoic acid is isolated by known techniques such as filtration.

The diastereomeric salt may optionally be crystallized to provide a pure product. The solvent for crystallization may be selected from a group of methanol, ethanol, isopropanol, tert-butanol, water, ethyl acetate, acetone, 1,4-dioxane, tetrahydrofuran and mixture thereof. Specifically, the solvent for crystallization is selected from a group of methanol, ethanol, isopropanol, tert-butanol, water and mixture thereof. More specifically, the solvent for crystallization is a mixture of isopropanol and water. The crude solid is mixed with the solvent and heated from about 40° C. to about 80° C. and specifically from about 50° C. to about 70° C. to dissolve the solid in the solvent. After complete dissolution of the solid in the solvent, the reaction mass is cooled from about –30° C. to about 10° C. and specifically from about –10° C. to about 0° C. The resulting solid is filtered to afford pure diastereomeric salt of (S)-3-(2,4-dihydroxyphenyl)-2-(4-hydroxyphenyl) propanoic acid.

One preferred embodiment of the present application relates to chiral amine salt of (S)-3-(2,4-dihydroxyphenyl)-2-(4-hydroxyphenyl)propanoic acid wherein the chiral amine may be selected from a group of N-tert-butylbenzylamine, N-benzylmethylamine, α-methylbenzylamine, α-ethylbenzylamine, 2-amino-3-methylbutane, N-octyl-D-glutamine, L-prolinol, cinchonidine, cinchonine, N-Boc-3-amino piperidine and 3-amino piperidine.

Another preferred embodiment of the present application relates to (S)-α-methylbenzylamine salt of (S)-3-(2,4-dihydroxyphenyl)-2-(4-hydroxyphenyl)propanoic acid of formula (8)

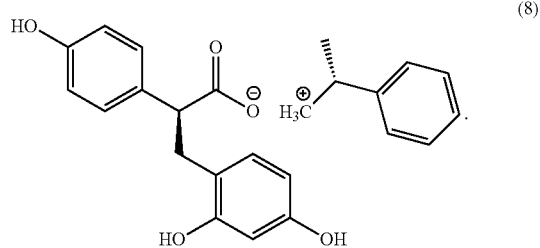

Yet another preferred embodiment of the present application relates to substantially pure (S)-α-methylbenzylamine salt of (S)-3-(2,4-dihydroxyphenyl)-2-(4-hydroxyphenyl)-propanoic acid (8). Substantially pure compound of formula (8) means that the compound is having at least about 95% diastereomeric purity (diastereomeric excess, d.e.) by HPLC. Specifically, the compound of formula (8) is having at least 97% diastereomeric purity by HPLC and more specifically the compound of formula (8) is having more than about 99% diastereomeric purity by HPLC.

Still another preferred embodiment of the present application relates to use of diastereomeric salt of (S)-3-(2,4-dihydroxyphenyl)-2-(4-hydroxyphenyl)propanoic acid for the preparation of (S)-equol (1).

Another preferred embodiment of the present application relates to use of (S)-α-methylbenzylamine salt of (S)-3-(2,4-dihydroxyphenyl)-2-(4-hydroxyphenyl)propanoic acid of formula (8) for the preparation of (S)-equol (1).

The chiral amine salt of (S)-3-(2,4-dihydroxyphenyl)-2-(4-hydroxyphenyl)propanoic acid wherein the chiral amine may be selected from a group of N-tert-butylbenzylamine, N-benzylmethylamine, α-methylbenzylamine, α-ethylbenzylamine, 2-amino-3-methylbutane, N-octyl-D-glucamine, L-prolinol, cinchonidine, cinchonine, N-Boc-3-amino piperidine and 3-amino piperidine may be treated with suitable acid in suitable solvent to provide (S)-3-(2,4-dihydroxyphenyl)-2-(4-hydroxyphenyl)propanoic acid of formula (7A). Specifically, (S)-α-methylbenzylamine salt of (S)-3-(2,4-dihydroxyphenyl)-2-(4-hydroxyphenyl)propanoic acid of formula (8) may be treated with suitable acid in suitable solvent to provide (S)-3-(2,4-dihydroxyphenyl)-2-(4-hydroxyphenyl)propanoic acid of formula (7A). The acid may be selected from a group of hydrochloric acid, hydrobromic acid, sulfuric acid, nitric acid, oxalic acid, acetic acid, propionic acid and phosphoric acid. Specifically, the acid is selected from a group of hydrochloric acid, sulfuric acid and nitric acid. More specifically, the acid is hydrochloric acid. The solvent may be selected from a group of esters, alcohols, ethers, water and mixture thereof. Specifically, the solvent is a mixture of ester solvent and water. More specifically, the solvent is a mixture of ethyl acetate and water. The organic solvent is separated from the aqueous phase and evaporated under vacuum to provide (S)-3-(2,4-dihydroxyphenyl)-2-(4-hydroxyphenyl) propanoic acid of formula (7A).

One preferred embodiment of the present application relates to (S)-3-(2,4-dihydroxyphenyl)-2-(4-hydroxyphenyl) propanoic acid of formula (7A)

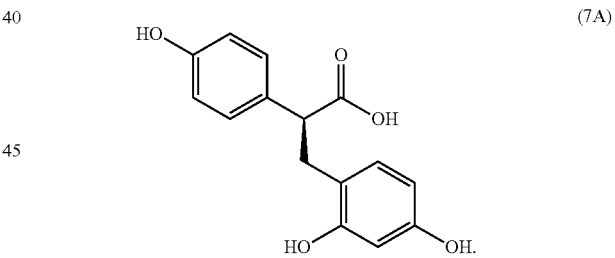

Another preferred embodiment of the present application relates to use of (S)-3-(2,4-dihydroxyphenyl)-2-(4-hydroxyphenyl)propanoic acid of formula (7A) in the preparation of (S)-equol (1).

Yet another preferred embodiment of the present application relates to substantially pure (S)-3-(2,4-dihydroxyphenyl)-2-(4-hydroxyphenyl)-propanoic acid (7A). Substantially pure compound of formula (7A) means that the compound is having at least about 95% enantiomeric purity (enantiomeric excess, e.e.) by HPLC. Specifically, the compound of formula (7A) is having at least 97% enantiomeric purity by HPLC and more specifically the compound of formula (7A) is having more than about 99% enantiomeric purity by HPLC.

The optically active acid of formula (7A) is reacted with a suitable reducing agent in presence of a solvent to provide (S)-4-(3-hydroxy-2-(4-hydroxyohenyl)propyl)benzene-1,3- diol of formula (9). The reducing agent may be selected from a group of borane and dimethyl sulfide complex ($BH_3$-DMS), sodium borohydride, lithium borohydride, lithium aluminum hydride, boron trifluoride etherate ($BF_3$:$Et_2O$), diisobutyl aluminum hydride and sodium bis(2-methoxyethoxy)aluminumhydride (REDAL). Specifically, the reducing agent is $BH_3$-DMS. The solvent may be selected from the group of methanol, ethanol, 1,4-dioxane, toluene, tetrahydrofuran, diethyl ether, diisopropyl ether and mixture thereof. Specifically, the solvent is selected from a group of 1,4-dioxane and tetrahydrofuran. More specifically, the solvent is 1,4-dioxane. A solution comprising optically active acid of formula (7A) in 1,4-dioxane is added to a mixture comprising 1,4-dioxane and $BH_3$-DMS. Alternatively, the mixture comprising 1,4-dioxane and $BH_3$-DMS may be added to the solution comprising optically active acid of formula (7A) in 1,4-dioxane. The reaction mass is heated to a temperature of 50° C. to about 200° C. for a period of about 2 hours to about 10 hours. Specifically, the reaction mass is heated to a temperature of 80° C. to about 150° C. for a period of about 4 hours to about 8 hours and more specifically reaction mass is heated to a temperature of 90° C. to about 95° C. for a period of about 5 hours to about 6 hours.

It has been surprisingly observed by the inventors of the present application that the reaction mass contains about 70% of desired alcohol of formula (9) along with about 30% of corresponding aldehyde of formula (10) after the completion of the reaction

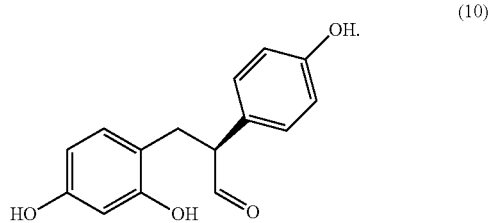 [SMILES: O=C[C@@H](Cc1ccc(O)cc1O)c1ccc(O)cc1]

(10)

In order to improve the yield and quality of the required product another suitable reducing agent is added to the reaction mass before work-up. The reducing agent is selected from a group of sodium borohydride, lithium borohydride and the like. Specifically, another reducing agent of the present application is sodium borohydride. The reaction is maintained for a period of about 30 minutes to about 3 hours after the addition of reducing agent. Specifically, the reaction mass is maintained for a period of about 1 hour to about 2 hours. The reaction mass is quenched by dilute hydrochloric acid and extracted with a water immiscible organic solvent. The water immiscible organic solvent may be selected from a group of toluene, chloroform, dichloromethane, methyl tert-butyl ether, diethyl ether and ethyl acetate. Specifically, the water immiscible organic solvent is ethyl acetate. The organic solvent is distilled off up to about 1 to about 2 volumes and dichloromethane is added to the product. The reaction mass is maintained from about 3 hours to about 10 hours and specifically maintained from about 5 hours to about 6 hours. The precipitated solid is isolated by filtration to afford (S)-4-(3-hydroxy-2-(4-hydroxyohenyl)propyl)benzene-1,3-diol of formula (9).

One preferred embodiment of the present application relates to (S)-4-(3-hydroxy-2-(4-hydroxyohenyl)propyl)benzene-1,3-diol of formula (9)

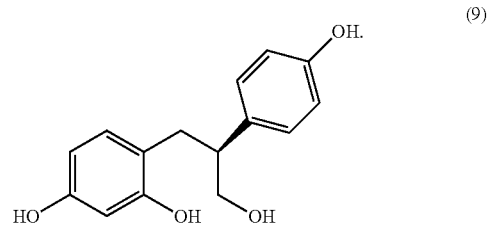 [SMILES: OC[C@@H](Cc1ccc(O)cc1O)c1ccc(O)cc1]

(9)

Another preferred embodiment of the present application relates to use of (S)-4-(3-hydroxy-2-(4-hydroxyohenyl)propyl)benzene-1,3-diol of formula (9) for the preparation of (S)-equol (1).

The alcohol of formula (9) can be cyclized under Mitsunobu conditions to provide (S)-equol (1). The solvent used for the reaction may be selected from a group of tetrahydrofuran, diisopropyl ether, 1,4-dioxane, methyl tert-butyl ether, dimethyl formamide, dimethyl acetamide and mixture thereof. Specifically, the solvent is tetrahydrofuran. To the reaction mass comprising alcohol of formula (9), triphenyl phosphine and suitable solvent, alkyl derivative of azodicarboxylate is added. The addition of azodicarboxylate may be in single lot or in several portions. The alkyl derivative of azodicarboxylate is selected from a group of diispropyl azodicarboxylate, diethyl azodicarboxylate and the like. Specifically, the alkyl derivative of azodicarboxylate is diispropyl azodicarboxylate. The reaction mass is maintained at a temperature of about 5° C. to about 25° C. for a period from about 30 minutes to about 3 hours. Specifically, the reaction mass is maintained at a temperature of about 15° C. to about 20° C. for a period from about 1 hour to about 2 hours. The reaction mass is quenched with an aqueous solution of lithium hydroxide and extracted with a water immiscible organic solvent to remove the side products. The water immiscible organic solvent may be selected from a group of ethyl acetate, diethyl ether, methyl tert-butyl ether, toluene and chloroform. Specifically, the water immiscible organic solvent is methyl tert-butyl ether. The aqueous layer is acidified with an acid. The acid may be selected from a group of hydrochloric acid, sulfuric acid, nitric acid and propionic acid. Specifically, the acid is dilute hydrochloric acid. The pH of the aqueous layer is adjusted from about pH 0.5 to about pH 5. Specifically, the pH of the aqueous layer is adjusted from about pH 1 to about pH 4. The reaction mass is maintained from about 2 hours to about 10 hours. Specifically, the reaction mass is maintained from about 3 hours to about 8 hours. More specifically, the reaction mass is maintained from about 5 hours to about 6 hours. The solid is isolated by filtration to provide (S)-equol (1). The isolated solid is optionally slurry washed with a solvent to provide a purified product. The suitable solvent is selected from a group of methanol, ethanol, isopropanol, tert-butanol, acetone, THF, 1,4-dioxane, water, acetic acid, propionic acid and mixture thereof. Specifically, the solvent is selected from a group of methanol, ethanol, isopropanol, tert-butanol, acetone, water and mixture thereof. More specifically, the solvent is a mixture of isopropanol and water. The reaction mass is maintained for a period from about 5 hours to about 20 hours. Specifically, the reaction mass is maintained for a period from about 7 hours to about 15 hours and more specifically maintained for a period from about 12 hours to about 14 hours. The solid is isolated by filtration to provide (S)-equol (1).

The process of the instant application has provided (S)-equol (1) with improved yield and improved chemical as well as enantiomeric purity when measured by HPLC technique. The process of the instant application provides more than about 22% of overall yield, much better than prior art processes.

(S)-equol (1) obtained by a process of instant application has chemical purity of more than about 95% when measured by HPLC technique. Specifically, (S)-equol (1) obtained by a process of instant application has more than about 97% purity and more specifically (S)-equol (1) obtained by a process of instant application has more than about 98% purity.

(S)-equol (1) obtained by a process of instant application has enantiomeric purity of more than about 95% when measured by HPLC technique. Specifically, (S)-equol (1) obtained by a process of instant application has more than about 97% enantiomeric purity and more specifically (S)-equol (1) obtained by a process of instant application has more than about 99% enantiomeric purity.

One embodiment of the present application relates to the pharmaceutical composition comprising (S)-equol (1) obtained by a process of instant application.

Certain specific embodiments will be further explained in the following examples, which are being provided only for the purpose of illustration, and the scope of this application is not limited thereto.

EXAMPLE 1

Synthesis of 4-(7-acetoxy-2-oxo-2H-chromen-3-yl) phenyl acetate (3)

To a mixture of 4-hydroxyphenyl acetic acid (50 g) and 2,4-dihydroxybenzaldehyde (45.46 g) acetic anhydride (250 mL) and diisopropylethylamine (200 mL) were added and the reaction mixture was heated at 115-120° C. for about 40±2 hours. The reaction mixture was then cooled to RT and then water (1000 mL) was added. The reaction mass was maintained at RT for 4-5 hours. The solid was filtered off, washed with water (250 mL) and dried at 70-75° C. for 12-14 hours to afford the title compound.

Yield: 103 g
$^1$H NMR 400 MHz, CDCl$_3$) δ: 2.33 (s, 3H), 2.35 (s, 3H), 7.06-7.09 (dd, J=8.4 Hz, J=2.4 Hz 1H), 7.15-7.20 (m, 3H), 7.54 (d, J=8.4 Hz, 1H), 7.71-7.75 (m, 2H), 7.79 (s, 1H).
MS: m/z=339.20 [M+1].

EXAMPLE 2

Synthesis of 7-hydroxy-3-(4-hydroxyphenyl)-2H-chromen-2-one (4)

To a solution of 4-(7-acetoxy-2-oxo-2H-chromen-3-yl) phenyl acetate of formula (3) (80 gm) in DMF (400 mL) an aqueous solution of lithium hydroxide (29.8 g, 0.71 mol) was added at RT and maintained at 60-70° C. for 1-2 hours. After the completion of the reaction, water (800 mL) and dilute hydrochloric acid (112 mL) was added to the reaction mass. The reaction mass was maintained at RT for 1-2 hours. The solid was filtered and dried at 70-75° C. for 6-8 hours to afford the title compound.

Yield: 57 g
$^1$H NMR (400 MHz, DMSO-d$_6$) δ: 6.75 (d, J=1.6 Hz, 1H), 6.79-6.83 (m, 3H), 7.53-7.58 (m, 3H), 8.02 (s, 1H), 9.66 (s, 1H), 10.55 (s, 1H).
MS: m/z=255.10 [M+1].

EXAMPLE 3

Synthesis of 7-hydroxy-3-(4-hydroxyphenyl)chroman-2-one (5) and methyl 3-(2,4-dihydroxyphenyl)-2-(4-hydroxyphenyl)propanoate (6)

To a solution of 7-hydroxy-3-(4-hydroxyphenyl)-2H-chromen-2-one (4) (57 gm) in DMF (320 mL) and methanol (320 mL), palladium-charcoal (6.4 g) was added. The reaction mixture was then hydrogenated at 8-10 bar hydrogen pressure at 60-65° C. for 12-16 hours till the reaction was completed. The reaction mixture was cooled to RT and palladium-charcoal was filtered off. The filtrate was distilled off under vacuum below 55° C. up to 5 volumes, and the crude concentrated reaction mixture was taken for the next stage of the process without any further work up or purifications.

Spectral data of
7-hydroxy-3-(4-hydroxyphenyl)chroman-2-one (5)

$^1$H NMR (400 MHz, DMSO-d$_6$) δ: 2.98-3.03 (m, 1H), 3.16-3.22 (m, 1H), 4.01-4.04 (m, 1H), 6.46 (d, J=2.0 Hz, 1H), 6.52-6.54 (dd, J=8.4 Hz, J=2.0 Hz 1H), 6.70 (d, J=8.4 Hz, 2H), 7.06-7.08 (m, 3H), 9.36 (s, 1H), 9.63 (s, 1H).
MS: m/z=257.20 [M+1].

Spectral data of methyl 3-(2,4-dihydroxyphenyl)-2-(4-hydroxyphenyl)propanoate (6)

$^1$H NMR (400 MHz, DMSO-d$_6$) δ: 2.73-2.78 (m, 1H), 2.97-3.03 (m, 1H), 3.49 (s, 3H), 3.79-3.82 (m, 1H), 6.00-6.03 (dd, J=7.6 Hz, J=1.6 Hz 1H), 6.23 (d, J=2.4 Hz, 1H), 6.61-6.68 (m, 3H), 7.04 (d, J=8.4 Hz, 2H), 8.96 (s, 1H), 9.20 (s, 1H), 9.30 (s, 1H).
MS: m/z=289.20 [M+1].

EXAMPLE 4

Synthesis of 3-(2,4-dihydroxyphenyl)-2-(4-hydroxyphenyl)propanoic acid (7)

Potassium hydroxide (39.76 g) in water (800 mL) was added to the crude mass obtained from example 3 at below 20° C. After the completion of the reaction, the pH of reaction mass was adjusted to 2-3 using dilute hydrochloric acid. The product was extracted by ethyl acetate (2×400 mL). The organic layer was washed with 10% brine solution (800 mL). The organic layer was distilled off under vacuum below 45° C. up to 1-1.5 volumes, and the crude concentrated reaction mixture was taken for the next stage of the process without any further work up or purification.
$^1$H NMR (400 MHz, DMSO-d$_6$) δ: 2.67-2.72 (m, 1H), 2.96-3.01 (m, 1H), 3.68-3.72 (m, 1H), 6.01-6.03 (dd, J=8.0 Hz, J=2.4 Hz 1H), 6.23 (d, J=2.8 Hz, 1H), 6.64-6.68 (m, 3H), 7.05 (d, J=8.4 Hz, 2H), 8.96 (s, 1H), 9.15 (s, 1H), 9.28 (s, 1H), 11.00-12.90 (b, 1H).
MS: m/z=275.20 [M+1].

EXAMPLE 5

Synthesis of (S)-α-methylbenzylamine salt of (S)-3-(2,4-dihydroxyphenyl)-2-(4-hydroxyphenyl)propanoic acid (8)

Isopropyl alcohol (IPA, 1040 mL) was added to the crude mass obtained from example 4 and distilled off under vacuum below 45° C. up to 11-12 volumes. (S)-(−)-α-methyl benzyl amine (25.7 g) was added to the reaction mass. The reaction mass was heated to 55-65° C. and maintained for 1 hr. The reaction mixture was then cooled to RT and maintained at that temperature for 5-6 hours. The product was filtered off and the crude product was taken in a mixture of IPA (5 vol) and water (5 vol). The reaction mass was heated to 55-65° C. and maintained for 1 hr. The reaction mixture was then cooled to −10° C. and maintained at that temperature for 5-6 hours. The solid was filtered off and dried at 70-75° C. for 6-8 hours to afford the title compound.

Yield: 26 g $^1$H NMR (400 MHz, DMSO-d$_6$) δ: 1.04 (d, J=6.4 Hz, 1H), 1.32 (d, J=8.0 Hz, 3H), 3.01-3.07 (m, 1H), 3.46-3.51 (m, 2H), 4.10-4.15 (m, 1H), 6.04-6.07 (dd, J=8.4 Hz, J=2.4 Hz 1H), 6.17 (d, J=2.4 Hz, 1H), 6.63-6.69 (m, 3H), 7.06 (d, J=8.8 Hz, 2H), 7.24-7.41 (m, 5H), 8.20-9.60 (b, 3H).

Chiral Purity (by HPLC): 99.5% d.e.

EXAMPLE 6

Synthesis of (S)-3-aminopiperidine salt of (S)-3-(2, 4-dihydroxyphenyl)-2-(4-hydroxyphenyl)propanoic acid (8A)

IPA (20 mL) was added to the crude mass obtained from example 4 and distilled off under vacuum below 45° C. up to 10 volumes. (S)-(−)-aminopiperidine hydrochloride (0.602 gm) was in-situ converted to free base with methanolic sodium hydroxide (0.27 gm) in methanol (15 mL), and the methanol was distilled off completely. To the residue, IPA solution of acid of formula (7) was added and the reaction mass was heated to 55-65° C. and maintained for 1 hr. The reaction mixture was then cooled to RT and maintained at that temperature for 5-6 hours. The solid was filtered off, washed with IPA (1 mL) and dried at 70-75° C. for 6-8 hours to afford the title compound.

Yield: 0.51 g

Chiral Purity (by HPLC): 64.8% d.e.

EXAMPLE 7

Synthesis of chinchonine salt of (S)-3-(2,4-dihydroxyphenyl)-2-(4-hydroxyphenyl)propanoic acid (8B)

IPA (20 mL) was added to the crude mass obtained from example 4 and distilled off under vacuum below 45° C. up to 9-10 volumes. Cinchonine (1.03 g) was added into the reaction mass. The reaction mass was heated to 55-65° C. and maintained for 1 hr. The reaction mixture was then cooled to RT and maintained at that temperature for 5-6 hours. The product was filtered off, washed with IPA (1 mL) and dried at 70-75° C. for 6-8 hours to afford the title compound.

Yield: 0.26 g

Chiral Purity (by HPLC): 36.9% d.e.

EXAMPLE 8

Synthesis of (S)-4-(3-hydroxy-2-(4-hydroxyphenyl) propyl)benzene-1,3-diol (9)

Dilute hydrochloric acid (25 mL) was added to a mixture of compound of formula (8A) (50 g) in ethyl acetate (250 mL) and water (250 mL). The aqueous layer was extracted with ethyl acetate (150 mL). The combined organic layer was washed with 10% brine solution (150 mL). The organic layer was distilled off under vacuum below 45° C. up to 1-1.5 volumes and re-distilled with 1,4-dioxane (2×50 mL) to afford (S)-3-(2,4-dihydroxyphenyl)-2-(4-hydroxyphenyl) propanoic acid as residue. The residue was dissolved in 1,4-dioxane (400 mL). It was added slowly into a mixture of BH$_3$:DMS (252 mL) in 1,4-dioxane (250 mL). After the addition was over, the reaction mass was maintained at 90-95° C. for 5-6 hours. Once the reaction was completed, the reaction mass was cooled to RT and methanol (150 mL) and sodium borohydride (3.58 g) was added. The reaction mass was maintained at RT for 1-2 hours. After the completion of the reaction, the reaction mass was acidified with dilute hydrochloric acid (25 mL) and distilled off under vacuum up to about 5 volumes. About 20% brine solution (250 mL) was added into the above reaction mass and extracted with ethyl acetate (2×250 mL). The organic layer was washed with bicarbonate solution followed by brine solution. The organic layer was distilled off under vacuum below 50° C. up to 1-2 volumes and added dichloromethane (500 mL). The reaction mass maintained at RT for 5-6 hours. The solid was filtered off and dried at 85-90° C. for 10-12 hours to afford the title compound.

Yield: 24 g $^1$H NMR (400 MHz, DMSO-d$_6$) δ: 2.77-2.89 (m, 2H), 3.45 (t, J=5.2 Hz 2H), 4.39 (t, J=5.6 Hz 1H), 5.99-6.02 (dd, J=8.0 Hz, J=2.4 Hz, 1H), 6.20 (d, J=2.4 Hz, 1H), 6.60 (d, J=8.4 Hz, 3H), 6.95 (d, J=8.4 Hz, 2H), 8.85 (s, 1H), 8.99 (s, 1H), 9.01 (s, 1H).

MS: M/Z=261.20 [M+1].

EXAMPLE 9

Synthesis of (S)-equol (1)

To a mixture of alcohol of formula (9) (50 g) and triphenyl phosphine (151 g) in THF (2.5 L) diisopropyl azodicarboxylate (116.5 g) in THF (500 mL) was added at 15-20° C. and maintained at that temperature for 1-2 hours. About 5% lithium hydroxide solution (1000 mL) was added into the reaction mass and extracted with MTBE (3×750 mL) to remove the organic impurities. The pH of the aqueous layer was adjusted to 1-4 by dilute hydrochloric acid (250 mL). The reaction mass was maintained at RT for 5-6 hours and the product was filtered off. The crude product was taken with IPA (7.5 vol) and added water (22.5 vol). The reaction mass was then maintained at RT for 12-14 hours. The solid was filtered and dried at 50-55° C. for 10-12 hours to afford the title compound.

Yield: 36 g

Chemical purity (by HPLC): 98.9%.

Chiral purity (by HPLC): 99.7% e.e.

$^1$H NMR (400 MHz, DMSO-d$^6$) δ: 2.50-2.87 (m, 2H), 2.97-3.34 (m, 1H), 3.86-3.92 (m, 1H), 4.13-4.16 (m, 1H), 6.18 (d, J=2.4 Hz, 1H), 6.27-6.29 (dd, J=8.0 Hz, J=2.0 Hz, 1H), 6.71 (d, J=8.8 Hz, 2H), 6.86 (d, J=7.6 Hz, 1H), 7.10 (d, J=8.4 Hz, 2H), 9.14 (s, 1H), 9.26 (s, 1H).

MS: m/z=243.10 [M+1].

We claim:

1. A process for the preparation of (S)-equol (1)

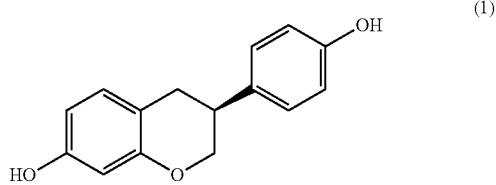 [SMILES: Oc1ccc([C@H]2COc3cc(O)ccc3C2)cc1]

comprising:

(a) reacting 4-hydroxy phenyl acetic acid and 2,4-dihydroxy benzaldehyde in presence of an acid anhydride and a base to provide 4-(7-acetoxy-2-oxo-2H-chromen-3-yl)phenyl acetate of formula (3)

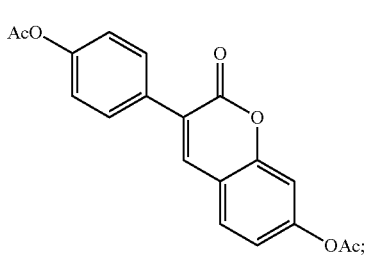
(3)

(b) hydrolyzing the acetyl groups of 4-(7-acetoxy-2-oxo-2H-chromen-3-yl)phenyl acetate of formula (3) in presence of a base to provide 7-hydroxy-3-(4-hydroxyphenyl)-2H-chromen-2-one of formula (4)

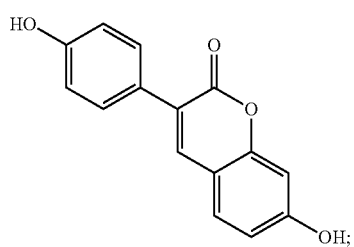
(4)

(c) hydrogenating 7-hydroxy-3-(4-hydroxyphenyl)-2H-chromen-2-one of formula (4) to provide a mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6)

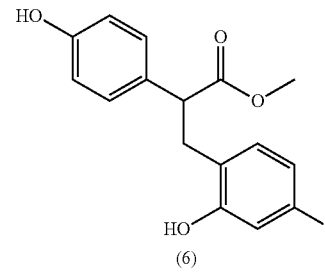
(5)

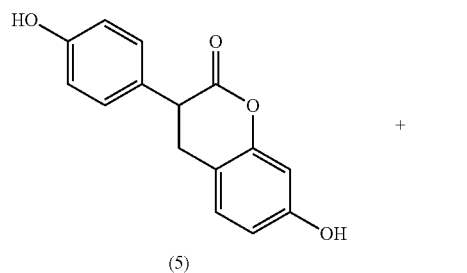
(6)

(d) hydrolyzing the mixture of 7-hydroxy-3-(4-hydroxyphenyl)-2H-chroman-2-one of formula (5) and methyl 3-(2,4-dihydroxyphenyl)-2-(4-hydroxyphenyl)propanoate of formula (6) with a base to provide 3-(2,4-dihydroxyphenyl)-2-(4-hydroxyphenyl)-propanoic acid of formula (7)

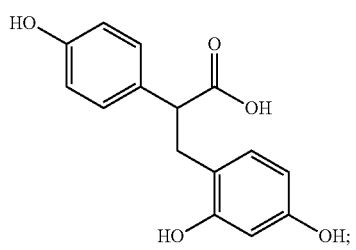
(7)

(e) resolving 3-(2,4-dihydroxyphenyl)-2-(4-hydroxyphenyl)propanoic acid of formula (7) to its corresponding (S)-isomer (7A) via diastereomeric salt formation with a chiral amine

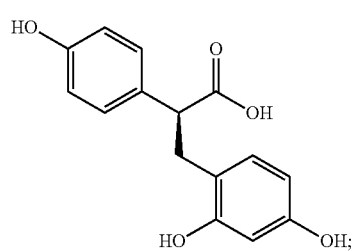
(7A)

(f) reducing (S)-3-(2,4-dihydroxyphenyl)-2-(4-hydroxyphenyl)propanoic acid of formula (7A) to provide (S)-4-(3-hydroxy-2-(4-hydroxyohenyl)propyl)benzene-1,3-diol of formula (9)

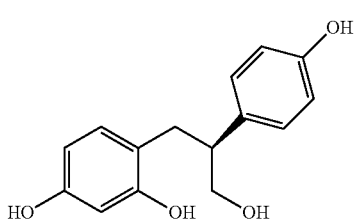
(9)

and
(g) cyclizing (S)-4-(3-hydroxy-2-(4-hydroxyohenyl)propyl)benzene-1,3-diol of formula (8) to provide (S)-equol (1).

2. The process of claim 1, wherein the acid anhydride of step (a) is acetic anhydride.

3. The process of claim 1, wherein the base of step (a) is diisopropylethylamine.

4. The process of claim 1, wherein the base of step (b) is lithium hydroxide.

5. The process of claim 1, wherein hydrogenation of step (c) is preformed in presence of a heterogeneous catalyst.

6. The process of claim 5, wherein the heterogeneous catalyst is palladium on charcoal.

7. The process of claim 1, wherein the base of step (d) is potassium hydroxide.

8. The process of claim 1, wherein the chiral amine of step (e) is selected from a group of N-tert-butylbenzylamine, N-benzylmethylamine, α-methylbenzylamine, α-ethyl-benzylamine, 2-amino-3-methylbutane, N-octyl-D-glucamine, L-prolinol, cinchonidine, cinchonine, N-boc-3-amino piperidine and 3-amino piperidine.

9. The process of claim 1, wherein the reducing agent of step (f) is borane and dimethyl sulfide complex ($BH_3$-DMS).

10. A compound, 3-(2,4-dihydroxyphenyl)-2-(4-hydroxyphenyl)propanoic acid of formula (7)

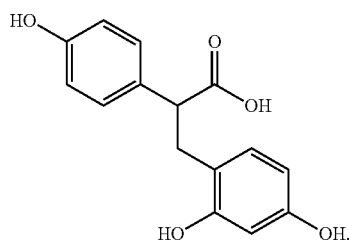

(7)

11. A compound, (S)-3-(2,4-dihydroxyphenyl)-2-(4-hydroxyphenyl)propanoic acid of formula (7A)

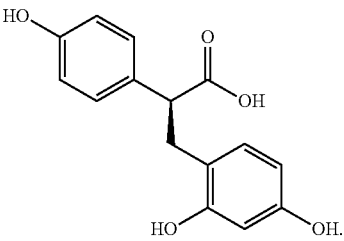

(7A)

12. A compound, (S)-α-methylbenzylamine salt of (S)-3-(2,4-dihydroxyphenyl)-2-(4-hydroxyphenyl)propanoic acid of formula (8)

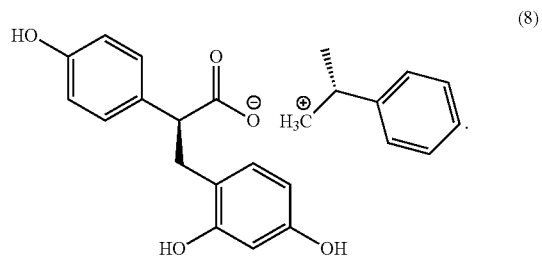

(8)

13. A compound, (S)-4-(3-hydroxy-2-(4-hydroxyohenyl)propyl)benzene-1,3-diol of formula (9)

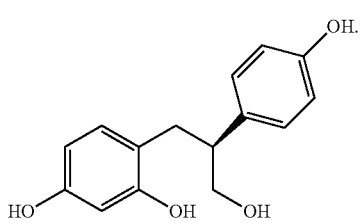

(9)

\* \* \* \* \*